United States Patent [19]
Kokubo et al.

[11] Patent Number: 4,948,622
[45] Date of Patent: Aug. 14, 1990

[54] METHOD FOR THE PREPARATION OF COATED SOLID MEDICAMENT FORM

[75] Inventors: Hiroyasu Kokubo; Hiroaki Muto; Tohru Chiba, all of Niigata, Japan

[73] Assignee: Shin-Etsu Chemical Co., Ltd., Tokyo, Japan

[21] Appl. No.: 224,772

[22] PCT Filed: May 23, 1988

[86] PCT No.: PCT/JP88/00483
§ 371 Date: Jun. 9, 1988
§ 102(e) Date: Jun. 9, 1988

[87] PCT Pub. No.: WO89/05635
PCT Pub. Date: Jun. 29, 1989

[30] Foreign Application Priority Data

Dec. 23, 1987 [JP] Japan .................................. 62-326589

[51] Int. Cl.$^5$ .............................................. A61K 9/00
[52] U.S. Cl. ...................................... 427/3; 424/476; 424/480; 424/494; 424/498
[58] Field of Search .................... 427/3; 424/476, 480, 424/494, 498

[56] References Cited

U.S. PATENT DOCUMENTS 2,540,979  2/1951  Clymer et al. ........................ 167/82

FOREIGN PATENT DOCUMENTS 0013566  7/1980  European Pat. Off. .
0164959  12/1985  European Pat. Off. .

Primary Examiner—Michael Lusignan
Attorney, Agent, or Firm—Wyatt, Gerber, Burke and Badie

[57] ABSTRACT

Solid medicament forms, such as granules, beads, tablets, are first coated with a hot aqueous dispersion of a cellulose ether, which is soluble in cold water but insoluble in hot water, and then subjected to a wax treatment with heating to form a masking layer of the wax. Different from the coating film of a cellulose ether formed by using an aqueous or organic solution of the cellulose ether, the coating film formed by using the aqueous dispersion of the cellulose ether has a porous structure so that the amount of the wax deposited in the wax treatment is much larger than in the prior art methods to exhibit a high effect of masking the bitterness of the ingredient contained in the medicament form.

5 Claims, 2 Drawing Sheets

METHOD FOR THE PREPARATION OF COATED SOLID MEDICAMENT FORM

FIELD OF TECHNOLOGY

The present invention relates to a method for the preparation of a coated solid medicament form. More particularly, the present invention relates to a method for the preparation of a coated solid medicament form capable of enhancing the effect of wax treatment of the solid medicament form after film coating and masking of unpleasant taste and having applicability to any types of solid medicament forms including granules and beads of a relatively small particle diameter.

BACKGROUND TECHNOLOGY

It is a generally practiced method in pharmaceutical preparation of perform film coating on various kinds of solid medicament forms such as tablets, granules, beads, capsules and the like by use of a water-soluble cellulose ether with an object of protecting the effective ingredients contained therein from atmospheric influences or increasing beautifulness in the appearance. Although certain cellulose ethers are soluble in organic solvents and a solution thereof in an organic solvent can be used as the coating solution on solid medicament forms, the use of organic solvents is disadvantageous and has problemsn in the pollution of the working environments and toxicity due to the residual amount of the solvent in the coating layer if not to mention the increase in the costs due to the expensiveness of organic solvents. In this regard, therefore, it is a trend in recent years that the process of film coating of solid medicament forms with a cellulose ether is prformed by use of an aqueous solution thereof which is directly sprayed on to the solid medicament forms.

In the following, a more detailed description is given of the film-coating of solid medicament forms by using an aqueous solution of a cellulose ether for the respective types of the medicament forms. When a sufficiently high masking effect is desired of tablets, in the first place, it was a traditional method to provide the tablets with sugar coating. In view of the low productivity of the complicated process of sugar coating, it is a trend in resent years that sugar coating is increasinly replaced with film coating of a water-soluble cellulose ether. Film-coated tablets with a water-soluble cellulose ether, however, have problems in respect of the insufficient masking effect and sliminess of the coating in the oral cavity of the person administrated with the tablets.

Solid medicament forms in the form of granules are conventionally provided with a coating of a water-soluble cellulose ether or an enterosuluble coating material. Granules coated with a water-soluble cellulose ether are usually not imparted with a full masking effect so that the person administered with the coated granules may sometimes feel bitterness in addition to stickiness in the oral cavity. In the enteric-coated granules, increase in the coating amount with an object to enhance the masking effect causes a problem in the decreased rate of releasing of the effective ingredients in the intestines.

Apart from the above, on the other hand, comsumption of solid medicament forms in the form of beads is increasing in recent years for the reasons in the medicament preparation or upgrading of medicament forms such as amplification of product assortment with the same effective ingredient. Accordingly, solid medicament forms conventionally prepared in the form of granules are sometimes converted into the form of beads or products of beads are added to the product assortment of granules. Conversion of granules into fine beads is naturally accompanied by a great increase in the surface area of the solid medicament form so that solutions must be sought for novel problems or for the problems already solved for granules by undertaking a coating method with a water-soluble cellulose ether or an enterosoluble coating material in connection with the process of medicament preparation such as the great increase in the coating amount or the time taken for coating in order to obtain a masking effect of the same degree as in granules and tablets. In particular, a problem in the coating procedure of fine beads by use of a conventional aqueous solution or organic solution is the difficulty in preventing agglomeration of particles in the course of the coating works.

Further, solid medicament forms are sometimes provided with wax coating. For examples, tablets are wax-coated without using any organic solvent or solution by adding a molten wax into the coating pan or by adding a fine powder of wax into the coating pan followed by heating. The amount of wax coating is, however, usually low and rarely exceeds 0.5% by weight on tablets because the purpose of wax coating is for glazing so that no masking effect can naturally be obtained by the wax coating. The amount of wax coating on granules and beads also does not exceed 5% by weight without exception and the method of wax coating thereon is limited to an ordinary method using a solvent.

As a method for film coating with a water-soluble cellulose ether, Japanese Patent Kokai 62-91272 teaches a method based on a principle that the viscosity of an aqueous solution of a hydroxypropyl cellulose is decreased by heating the aqueous solution. This method, however, is not applicable when the aqueous solution of the cellulose ether has a high viscosity as is the case when the aqueous solution contains the cellulose ether in a high concentration or the cellulose ether has a high degree of polymerization.

DISCLOSURE OF THE INVENTION

In connection with the above described problems, the inventors have previously proposed a method for the preparation of a coated solid medicament form in which a solid medicament form is coated by using a coating liquid which is a hot aqueous dispersion of a fine powder of a cellulose ether, which is soluble in cold water but insoluble in hot water. The method of the present invention has been established as a further improvement of this previously proposed method.

Thus, the method of the present invention for the preparation of a coated solid medicament form comprises the steps of:

(a) coating a solid medicament form by using a hot aqueous coating liquid which is an aqueous dispersion of a powder of a cellulose ether, which is insoluble in hot water but soluble in cold water, in hot water; and (b) subjecting the coated solid medicament form obtained in the step (a) to a heat treatment in the presence of a wax.

In particular, the above mentioned cellulose ether soluble in cold water but insoluble in hot water is selected from the group consisting of hydroxypropyl methyl cellulose, methyl cellulose, hydroxypropyl cellulose and hydroxyethyl methyl cellulose and the wax is selected from the group consisting of paraffin waxes, beeswaxes, higher alcohols, higher fatty acids, esters of higher fatty acids, glycerin fatty acid esters and polyethylene glycols.

BEST MODE EMBODIMENTS TO PRACTICE THE INVENTION

As is described above, the first step of the invention method is to provide the solid medicament form with a film-coating layer of a cellulose ether which is soluble in cold water but insoluble in hot water. Examples of suitable cellulose ethers include hydroxypropyl methyl cellulose, methyl cellulose, hydroxypropyl cellulose, hydroxyethyl methyl cellulose and the like. These cellulose ethers can be used either singly or as a mixture of two kinds or more according to need.

The coating liquid used in step (a) of the inventive method is a hot aqueous dispersion of the cellulose ether in a finely divided powdery form. Such a coating liquid can be prepared by dispersing the powdery cellulose ether in hot water at a temperature of, for example, about 80° C. and keeping the aqueous dispersion at a temperature of, for example, 60° C. or higher at which the cellulose ether is insoluble in water and can be kept in water without being dissolved under continued agitation.

The aqueous dispersion as the coating liquid used in the inventive method should contain the powdery cellulose ether in an amount in the range from 5 to 30% by weight or, preferably, from 5 to 15% by weight. When the content of the cellulose ether in the coating liquid is excessively high, difficulties are caused in the agitation of the aqueous dispersion so that uniformity of dispersion of the powder of cellulose ether cannot be ensured and the powder may eventually settle in the coating liquid sometimes to cause clogging of the spray gun nozzles. When the content of the powdery cellulose ether is too low in the coating liquid, a desired thickness of the coating film can be obtained only by unduly extending the time for the coating procedure with an economical disadvantage of low productivity.

It is optional that the aqueous dispersion of the powdery cellulose ether as the coating liquid used in the inventive method is further admixed according to need with various kinds of known additives conventionally used in coating of solid medicament forms including coloring agents such as edible dyes, edible lake pigments, titanium dioxide and the like, extender pigments such as talc, finely divided silica powder and the like, plasticizers such as polyethylene glycol, propylene glycol, glycerin, triethyl citrate, dibutyl phthalate and the like, flavors such as vanilla extract, orange oil and the like, and so on. Further, stability of the dispersion can be increased by adding a water-soluble polymer which is not insoluble in hot water in such a limited amount as not to cause troubles in the coating works by spraying of the coating liquid. Similarly, saccharides such as lactose, saccharose, mannose and the like can be added to the liquid as a water-soluble ingredients.

When the coating liquid is admixed wtih an additive which is insoluble in water, such as talc, titanium dioxide, water-insoluble polymers and the like, it is important that the amount of the powdery cellulose ether dispersed in the coating liquid is decreased correspondingly so that the overall solid content in the coating liquid may not be excessively high not to cause troubles in the coating works.

The coating works of solid medicament forms such as tablets, pills, granules, beads, capsules and the like with the above described coating liquid can be performed by use of any of conventional coating machines used in the pharmaceutical industry. Examples of suitable coating machines include rotating drum-type coaters such as Accelacota manufactured by Manesty Co., England, fluidized coaters such as those of Wurster type developed by Wisconsin University Foundation, U.S.A., and fluidized coaters manufactured by Glatt Co., West Germany. In practicing the coating works according to the inventive method, these coating machines can be operated under about the same conditions as in conventional coating works.

In contract to the dense coating films obtained in conventional coating procedures using a polymer which may be soluble in water or in organic solvents, the coating film obtained in step (a) of the inventive method described above has a considerable porosity which serves to exhibit an anchoring effect for the overcoating film of the wax formed in step (b) of the inventive method so that the bonding strength of the overcoating film of the wax to the underlying coating film of the cellulose ether can be greatly improved.

Various kinds of waxy materials can be used as the was used in step (b) of the inventive method as an overcoating on the coating film of the cellulose ether. Examples of suitable wax materials include hydrocarbon waxes such as paraffins and petrolatums, beeswaxes, i.e. bleached and unbleached beeswaxes, higher alcohols such as cetyl alcohol and stearyl alcohol, higher fatty acids such as stearic acid, esters of higher fatty acids such as carnauba wax and rice wax, fatty acid esters of glycerin such as beff tallow, lard, hardened soybeam oil and hardened castor oil and polyethylene glycols such as PEG-6000 and PEG-20000 as well as various commerical products sold under the tradenames of Lubri Wax-101, which is a hydrogenated vegetable oil, Polishing Wax-101, which is a mixture of carnauba wax and paraffin, Prectrol, which is a mixture of mono-, di-, and tripalmitates of glycerin, and the like, of which paraffin waxes and beeswaxes are preferred in respect of the strong hydrophobicity and high masking effect obtained therewith. These wax materials can be used either singly or as a mixture of two kinds of more according to need.

In particular, the wax material used in step (b) of the inventive method should have a melting point in the range from 40° to 90° C. or, preferably, in the range from 55° to 70° C. When the melting point of the wax is too low, the particles of the wax-coated solid medicament form may be subject to agglomeration even under ordinary conditions of storage. When the melting point of the wax is too high, the treatment by melting the wax muxt be performed at an unduly high temperature in order to smoothly and evenly spread the wax over the surface of the solid medicament form.

The wax material should preferably be in a finely divided form when the wax treatment is performed by using a coating pan and the wax powder is introduced into the coating pan and sprinkled over the solid medicament form under heating so that the wax is melted and spread over the surface of the solid medicament form. When the wax treatment is performed by using a fluidized coating machine, on the other hand, the wax material should have a particle size larger than the particles of the solid medicament form under the wax treatment since otherwise the particles of the wax may eventually be blown away during fluidization. For example, the wax material should preferably be in a granular form having a particle diameter of a few millimeters to facilitate handling.

The wax treatment of tablets under heating can be performed in a manner similar to conventional polishing methods with waxes. The wax jpowder is preferably sprinkled in several portions in order to increase the utilized amount of the wax introduced. When the solid medicament form is in the form of granules or beads, it is a convenient way to perform the wax treatment directly following the film coating with the cellulose ether and drying in the same fluidized coating machine. In this way, the particles of wax and the coated particles of the solid medicament form are mixed together in the fluidized bed by means of the hot fluidizing air so that the wax is melted and spread over the surface of the particles of the solid medicament form to exhibit the desired masking effect.

When the film coating of solid medicament forms with a collulose ether is performed by using a solution of the celluslose ether, the coating film of the cellulose ether is usually dense or has a smooth surface so that the amount of the deposited wax on the coating film in the subsequent wax treatment is only about 1 to 2% by weight though dependent on the particle size of the solid medicament form. In the method of the present invention, in contrast thereto, the coating of the solid medicament form with a cellulose ether is performed by using an aqueous dispersion of the cellulose ether particles as the coating liquid to give a coating film having a more or less porous surface so that the amount of the deposited wax material in the subsequent wax treatment can be as large as about 5 to 20% by weight though naturally dependent on the conditions of the wax treatment and the particle size of the solid medicament form. Moreover, the layer of the wax spread on the surface of the solid medicament form is not uniform over the whole surface but is very thin in spots to facilitate dissolution of the coating film of the cellulose ether and release of the effective ingredient from the solid medicament form after administration of the medicament. When the wax treatment is undertaken with an object of masking of bitterness of the effective ingredient, the amount of the coating wax required for masking can be not so large as to greatly retard releasing of the effective ingredient. Accordingly, it is a possible way to prepare a substained-release solid medicament form by increasing the amount of the coating wax according to the object of the medicament preparation.

In the following, examples are given to illustrate the method of the invention in more detail but not to limit the scope of the invention in any way. In the examples, the terms of "parts" and "%" always refer to "parts by weight" and "% by weight", respectively. In some of the following example, description is made with reference to the accompanying drawing.

EXAMPLE 1

Preparation of Granules for Coating

Figure 1:
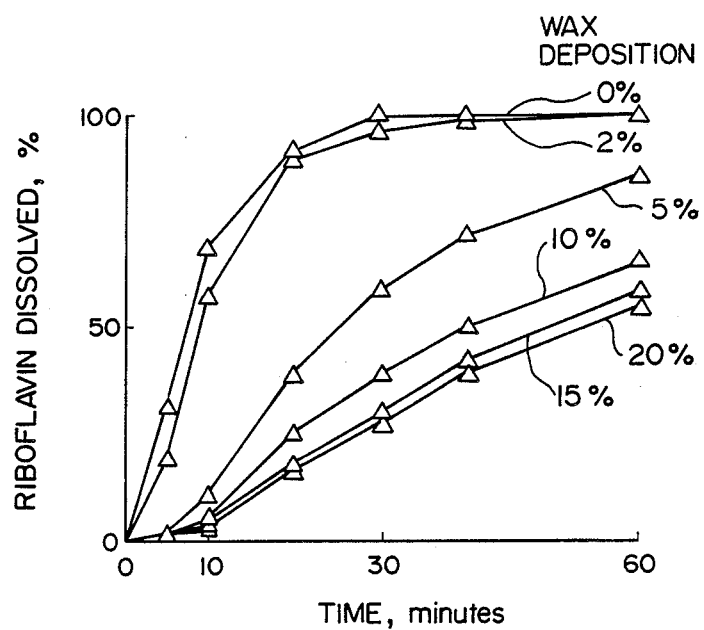
FIGS. 1 and 2 are each a graphic showing of the results of the dissolution tests of the riboflavin from the coated granules prepared in Example 2 with the amount of deposited wax as the parameter taking the dissolved amount in % as the ordinate and the testing time in minutes as the abscissa.

Columnar granules were prepared from a blend of 2 parts of riboflavin, i.e. vitamin $B_2$ (a product by Tokyo Tanabe Steiyaku Co.), 70 parts of lactose, 17 parts of corn starch, 5 parts of polyethylene glycol PEG-600 (a product by Nippon Yushi Kogyo Co.), 5 parts of a low-substitution hydroxypropyl cellulose (HPC-LEP, a product by Shin-Etsu Chemical Co.) and 1 part of a hydroxpyropyl cellulose (LH-21, a product of the same company as above) with addition of a small volume of water by extrusion through a screen of 1 mm opening using an extrusion granulator. The granules were subjected to a rounding treatment and then drying at 80° C. for 2 hours in a fluidized drying machine followed by sorting relative to the particle size using #12 and #50 screens specified in Japanese Pharmacopoeia.

Preparation of Coating Liquid

A coating liquid was prepared by adding 10 parts of a methyl cellulose of which a 2% by weight aqueous solution had a viscosity of 16.5 centipoise at 20° C. (SM-15, a product by Shin-Etsu Chemical Co.) in a powdery form to 90 parts of pure water at 80° C. and dispersing the powder with thorough agitation. The thus prepared coating liquid was kept at 50° C. without being cooled to a lower temperature throughout until it was used in the coating works.

Coating of the Granules

The coating machine used was a Glatt Fluidized coater (Model VSG-1, manufactured by Ohkawara Seisakusho Co.). The coating work was performed by introducing 1 kg of the base granules prepared above into the coating machine under the conditions of: temperature of the fluidizing air at 80° C.; temperature of the exhaust at 42° to 48° C.; and feed rate of the coating liquid of 50 g/minute, until the amount of the coating film reached 50% relative to the base granules. After completion of coating, the coated granules were dried for 30 minutes as they were in the fluidized coater with the fluidizing air at 80° C. Thereafter, 200 g of bleached beeswax having a melting point of 60° to 67° C. specified in Japanese Pharmacopoeia were introduced into the coating machine in several portions and a wax treatment was performed with heating under the same fluidizing conditions as above.

Evaluation of the Coated Granules

Electron microscopic photographs were taken of the base granules before the above described coating procedure and the coated granules to examine the surface condition of the graunules. As is clearly shown by the comprison of the photographs, the surface of the granules coated by using the aqueous dispersion of the cellulose ether had a network-like appearance with porosity. This surface condition was very effective in increasing the amount of the deposited wax in the subsequent wax treatment with heating to give an amount of wax deposition as high as 19% corresponding to a wax utilization of 95%.

COMPARATIVE EXAMPLE 1

Preparation of Coating Liquid

With an object to make a comparison with coating using an aqueous solution of a cellulose ether, a coating liquid was prepared by adding 5 parts of the same methyl cellulose as used in Example 1 to 95 parts of water at 80° C. and the powder was dispersed therein with agitation followed by cooling to 20° C. to dissolve the particles of the cellulose ether in water.

Coating of the Granules

The coating machine and the conditions of the coating work were the same as in Example 1 expecting the use of the above prepared aqueous solution as the coating liquid instead of the aqueous dispersion and decrease of the feed rate of the coating liquid to 35 g/minute in order to prevent agglomeration of the granules. The coating amount with the cellulose ether was the same as in Example 1 and the wax treatment was undertaken also in the same manner as in Example 1.

Evaluation of the Coated Granules

The procedure of wax treatment could no longer be continued when the amount of the deposited wax reached 2% due to interruption of the fluidization to cause agglomeration of the granules. The coated granules before the wax treatment were electron-microscopically examined to give a photograph which showed that the coating film had a smooth surface. This surface condition of the coated granules led to a remarkably small amount of wax deposition in comparision with Example 1 which was only about 2.5% at the largest.

EXAMPLE 2

Preparation of Coating Liquid

Two aqueous dispersions of different types of cellulose ethers to be used as the coating liquid were prepared each by adding 5 parts of a methyl cellulose of which a 2% aqueous solution had a viscosity of 3850 centipoise at 20° C. (SM-4000, a product by Shin-Etsu Chemical Co.) or a hydroxypropyl methyl cellulose of which a 2% aqueous solution had a viscosity of 4090 centipoise at 20° C. (60SH-4000, a product by the same company as above) to 95 parts of pure water at 80° C. and thoroughly agitating the mixture to disperse the cellulose ether particles. Each of the thus prepared coating liquids was kept at 50° C. without being cooled to a lower temperature throughout until it was used in the coating works.

Coating of the Granules

The same base granules as prepared and used in Example 1 were coated with the above prepared coating liquids in the same coating machine under the same conditions until the amount of the coating film reached 50% based on the base granules. The conditions of the wax treatment were about the same as in Example 1 excepting the use of varied amounts of a paraffin wax having a melting point of 60° to 62° C. (a product by Wako Junyaku Kogyo Co.) to give coated and wax-treated granules with varied amounts of wax deposition of 2%, 5%, 10% and 20%.

Evaluation of the Coated Granules

Each of the above obtained preparations of the coated granules was subjected to the dissolution test under the conditions shown below according to the procedure specified in Japanese Pharmacopoeia.
Test solution: first fluid, 900 ml
Amount of coated granules taken: 1 g
Testing method: paddle method, 100 rpm
Temperature: 37° C.

Figure 2:
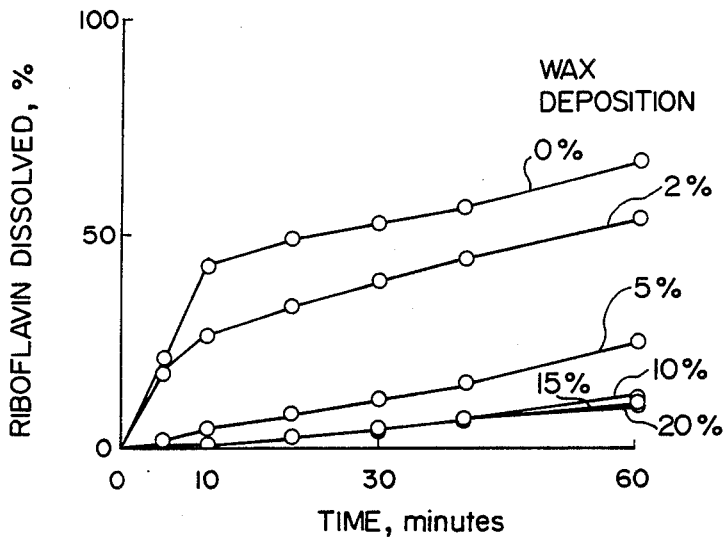

The amount of dissolved riboflavin was determined spectrophotometrically by the measurement of the maximum absorption of light at a wavelength of 444 nm. The reuslts are shown in FIGS. 1 and 2 for methyl cellulose and hydroxypropyl methyl cellulose, respectively, as the coating material on the base granules. As is understood from these figures, increase in the amount of the deposited wax had an effect to retard the rate of dissolution of the ingredient out of the coated granules.

EXAMPLE 3

Preparation of Beads for Coating

Beads were prepared by rolling granulation of a blend composed of 70 parts of lactose, 22 parts of corn starch, 0.5 parts of propantheline bromide (a product by Eizai Co.), 4.5 parts of a low-substitution hydroxypropyl cellulose (LH-31, product by Shin-Etsu Chemical Co.) and 3 parts of a hydroxypropyl cellulose (HPC-LEP, a product by the same company as above) with addition of a small volume of water followed by drying by fluidization and storing relative to the particle size using #30 and #83 screens specified in Japanese Pharmacopoeia.

Coating of the Beads

The above prepared beads were coated by using the same coating liquid and the same coating machine and under about the same conditions as in Example 1 expecting the use of a finer mesh screen of #100 for the fluidized bed until the amount of the coating film on the beads reached 50% based on the uncoated beads. The wax treatment of the thus coated beads was undertaken by using varied amounts of the same paraffin wax as used in Example 2 to give wax-treated beads with varied amounts of the deposited wax of 2%, 5%, 10% and 15%. The wax utilization was 95% in each of the wax treatment with varied amounts of wax deposition.

Evaluation of the Coated Beads

Each preparation of the coated and wax-treated beads and the coated beads before the wax treatment was subjected to an organoleptic test for bitterness undertaken by four testing members. Thus, a 500 mg portion of the sample beads put into the oral cavity of the testing member was kept there for 30 seconds and then swallowed down together with 100 ml of water to record the degree of bitterness felt by each member due to the propantheline bromide in three ratings expressed by the symbols of ±, + and ++. The results are shown in the table below.

TABLE

|  |  | Testing member | | | |
| --- | --- | --- | --- | --- | --- |
|  |  | A | B | C | D |
| Amount of | 0% | ++ | ++ | ++ | ++ |
| wax | 2% | + | + | + | + |
| deposition | 5% | + | + | + | + |
|  | 10% | ± | + | ± | ± |
|  | 15% | ± | ± | ± | ± |

±: absolutely no bitterness felt
+: bitterness felt slightly after swallowing
++: bitterness felt immediately by putting the medicament into mouth

EXAMPLE 4

Preparation of Tablets for Coating

Tablets each weighing 200 mg were prepared by using a pelletizing die and a punch of 8 mm diameter from a blend composed of 70 parts of lactose, 25 parts of corn starch and 4.5 parts of a low-substitution hydroxypropyl cellulose (LH-11, a product by Shin-Etsu Chemical Co.) with subsequent admixture of 0.5 part of magnesium stearate.

Preparation of Caoting Liquid

An aqueous dispersion was prepared by adding 5 parts of talc and 10 parts of a hydroxypropyl methyl cellulose of which a 2% aqueous solution had a viscosity of 6.1 centipoise at 20° C. (TC-5R, a product by Shin-Etsu Chemical Co.) to 85 parts of water at 80° C. and thoroughly agitating the mixture. The thus prepared aqueous dispersion as the coating liquid was kept at 80° C. without being cooled to a lower temperature throughout until it was used in the coating works.

Coating of Tablets

A small drum-type coating machine was used for coating of 1 kg of the above prepared tablets with the coating liquid at a feed rate of 12 g/minute at 80° C. of the intake air temperature and 40° to 45° C. of the exhause temperature to give a coating amount of 10%. After completion of coating, the tablets were dried for 30 minutes at 70° C. of the intake air temperature directly followed by a wax treatment by putting 50 g of a polishing wax in several portions with interruption of the air supply.

Evaluation of the Caoted Tablets

The coated tablets obtained in the above described manner were election-microscopically examined to give a photograph from which it was clear that the coated tablets had a porour surface like the coated granules prepared in Example 1 so that the amount of the wax deposited in the wax treatment could be as large as 5%.

COMPARATIVE EXAMPLE 2

Preparation of Coating Liquid

Instead of the aqueous dispersion of the cellulose ether and talc prepared and used in Example 4, a coating liquid was prepared by dispersing 5 parts of the same hydroxypropyl methyl cellulose and 2.5 parts of talc in 92.5 parts of pure water at 80° C. followed by cooling to 30° C. so as to dissolve the cellulose ether in water.

Coating of Tablets

Coating of the tablets prepared in Example 4 by using the above prepared coating liquid and subsequent wax treatment were performed in substantially the same manner as in Example 4. Since the solid content in the coating liquid was a half of that in the coating liquid used in Example 4, the time taken for the coating work was extended to twice of that in Example 4 so as to give the same coating amounts as in Example 4.

Evaluation of the Coated Tablets

The coated and was-treated tablets obtained in the above described manner were subjected to an electron-microscopic examination to give a photograph from which it was clear that the coating film had a more dense structure than in Example 4 with higher smoothness of the surface so that the amount of the deposited wax could hardly be increased over 1%. When an attempt was made to increase the amount of wax deposition over 1% by using an excessive amount of the polishing wax, small bumps of the wax were formed on the surface of the tablets so that no uniform layer of the wax could be obtained.

EXAMPLE 5

Beads of Coating

A commercial product of aspirin (Aspirin S, a product by Mitsui Toatsu Kagaku Co.) was used as such as the beads subjected to the coating treatment.

Preparation of Coating Liquid

An aqueous dispersion as the coating liquid was prepared by adding 10 parts of the same hydroxypropyl methyl cellulose as used in Exmaple 4, 2 parts of lactose, 2 parts of talc and 1 parts of a polyethylene glycol PEG-4000 (a product by Nippon Yushi Kogyo Co.) to 85 parts of pure water at 80° C. and thoroughly agitating the mixture. The thus prepared coating liquid was kept at 80° C. without being cooled to a lower temperature until it was used in the coating works.

Coating of the Beads

The beads were coated with the above prepared coating liquid using the same coating machine and under the same conditions as in Example 3 except that the coating amount was 40% calculated for the cellulose ether followed by a wax treatment using varied amounts of cetyl alcohol having a melting point of 49° C. (a product by Wako Junyaku Kogyo Co.) as the wax under about the same conditions as in Example 3 to give the amounts of wax deposition of 2%, 5% and 10%.

Evaluation of the Coated Beads

Figure 3:
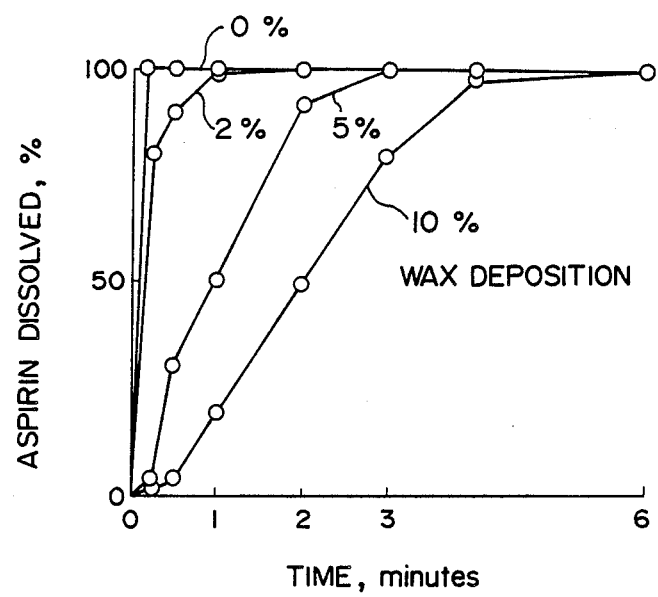
FIG. 3 is a similar graphic showing to FIGS. 1 and 2 for the coated beads of aspirin prepared in Example 5.

The coated and wax-treated beads of aspirin obtained in the above described manner were subjected to a dissolution test in a similar manner to Example 2. The amount of the dissolved aspirin was determined spectrophotometrically by the measurement of the maximum absorption of light due to aspirin at a wavelength of 276 nm. The results are shown in FIG. 3, from which it was understood that increase in the amount of the deposited cetyl alcohol had an effect of retarding dissolution of aspirin out of the coated beads.

POSSIBILITY OF INDUSTRIAL UTILIZATION

The method of the present invention provides a possibility of greatly improving the productivity in the coating works of solid medicament forms by viture of the decrease in the time taken for the coating works in comparison with conventional coating methods in which the coating liquid is an aqueous solution of a cellulose ether and not an aqueous dispersion of the same. In addition, the coating film of the cellulose ether formed by the inventive method on the surface of the solid medicament form has a porous surface condition so that the amount of wax deposition thereon can be remarkably increased in comparison with the amount on a dense and smooth surface formed by the conventional method.

The method of the present invention provides a solution of the problems in the conventional method using an aqueous or organic solution of a cellulose ether as the coating liquid that the coating method is not applicable to solid medicament forms of a relatively fine particle size distribution such as beads due to the extremely low productivity and that the amount of the wax deposited thereon cannot be high enough rarely to exceed 1 to 2%. Namely, the method of the invention is applicable to any type of solid medicament forms and the amount of wax deposition can be as high as 5 to 20% so that a perfect masking effect can be reafdily obtained. It is of course that the inventive method is absolutely free from the problem due to a residual amount of organic solvents in the coated solid medicament form because no organic solvent is used in the coating works.

The conventional coating method by using an enterosoluble coating material is not applicable to a solid medicament form for which rapid releasability of the effective ingredient is desired because the coating film may be imparted with enteric solubility when the coating amount exceeds a certain level. In contrast thereto, the method of the present invention is free from such a problem because the wax treatment to exhibit a sufficiently high masking effect has little adverse effect of retarding dissolution of the effective ingredient out of the coated solid medicament form.

We claim:

1. A method for the preparation of a coated solid medicament form which comprises the steps of:

(a) coating a solid medicament form by using a coating liquid which is an aqueous dispersion of a powder of a cellulose ether, which is insoluble in hot water butsoluble in cold water, in hot water; and
   (b) subjecting the coated solid medicament form obtained in the step (a) to a heat treatment in the presence of a wax.

2. The method for the preparation of a coated solid medicament form as claimed in claim 1 wherein the cellulose ether, which is insoluble in hot water but soluble in cold water is selected from the group consisting of hydroxypropyl methyl cellulose, methyl cellulose, hydroxypropyl cellulose and hydroxyethyl methyl cellulose.

3. The method for the preparation of a coated solid medicament form as claimed in claim 1 wherein the wax is selected from the group consisting of paraffin waxes, beeswaxes, higher alcohols, higher fatty acids, estes of higher fatty acids, fatty acid esters of glycerin and polyethylene glycols.

4. The method for the preparation of a coated solid medicament form as claimed in claim 1 wherein the aqueous dispersion of a powder of the cellulose ether contains from 5 to 30% by weight of solid.

5. The method for the preparation of a coated solid medicament form as claimed in claim 1 wherein the wax has a melting point in the range from 40° to 90° C.

* * * * *